United States Patent [19]

De Jonckheere

[11] 4,210,143

[45] Jul. 1, 1980

[54] DISPOSABLE NAPPY FOR A BABY

[75] Inventor: Raphaël De Jonckheere, Bondues, France

[73] Assignee: Societe Anonyme dite: Consortium General Textile, Nord, France

[21] Appl. No.: 927,977

[22] Filed: Jul. 26, 1978

[30] Foreign Application Priority Data

May 8, 1978 [FR] France .................... 78 14350

[51] Int. Cl.² ............................. A61F 13/16
[52] U.S. Cl. ................................. 128/287
[58] Field of Search ............... 128/284, 286, 287

[56] References Cited

U.S. PATENT DOCUMENTS

| 2,573,903 | 11/1951 | Gordon | 128/287 |
| 3,417,751 | 12/1968 | Murdoch | 128/284 |
| 3,426,756 | 2/1969 | Romanek | 128/287 |
| 3,658,063 | 4/1972 | Schaar | 128/287 |
| 3,865,111 | 2/1975 | Brooks | 128/287 |

Primary Examiner—Robert W. Michell
Assistant Examiner—C. F. Rosenbaum
Attorney, Agent, or Firm—Robert E. Burns; Emmanuel J. Lobato; Bruce L. Adams

[57] ABSTRACT

A disposable nappy for a baby comprises at least one sheet of flexible impermeable material comprising two longitudinal edges intended to define the openings for the baby's legs and two transverse edges intended to define a waist portion and an absorbent pad superimposed on a central region of the impermeable sheet. The nappy is characterised in that it comprises respectively in the immediate vicinity of each of the longitudinal edges; on either side of the pad, a flexible longitudinal sheath inside which a flexible longitudinal tie is able to slide and in that each sheath comprises means for gaining access to the corresponding flexible tie in order to enable the latter to be gripped manually and to be tensioned at will in order to reduce the apparent length of the longitudinal edges; to press the latter at will around the baby's legs and to give the disposable nappy the shape of a trough, between the latter.

5 Claims, 4 Drawing Figures

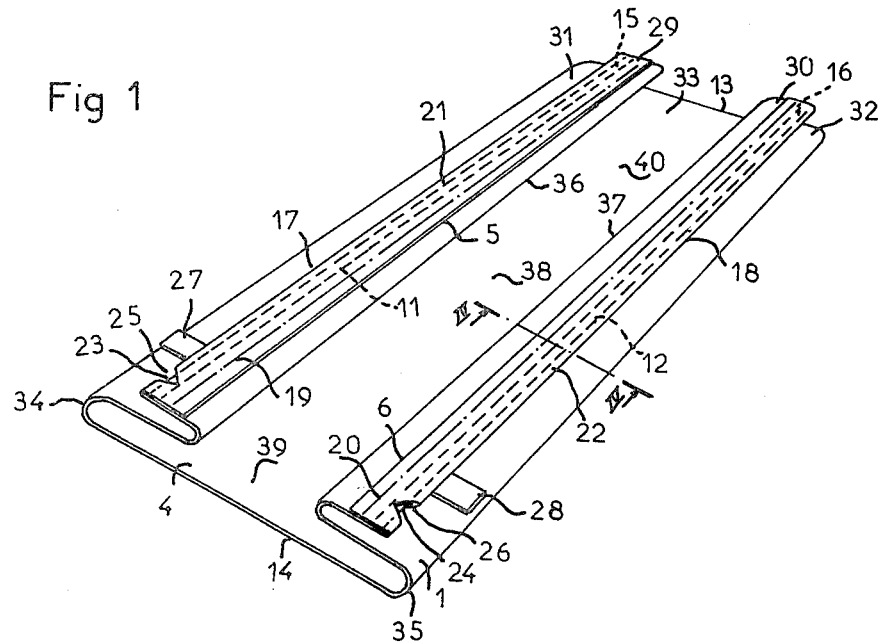
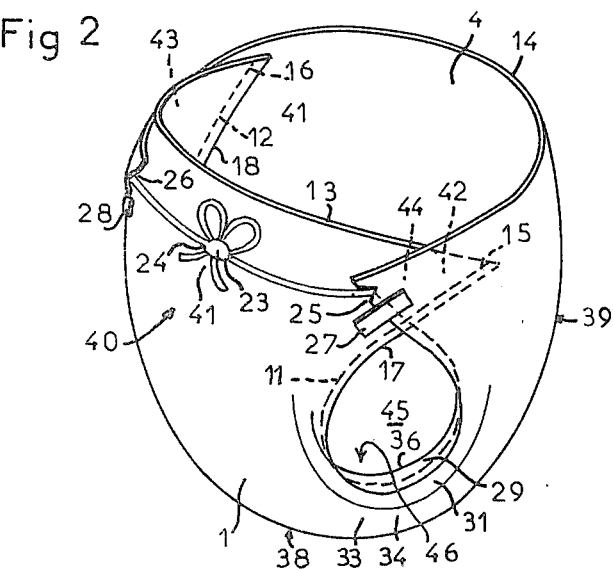

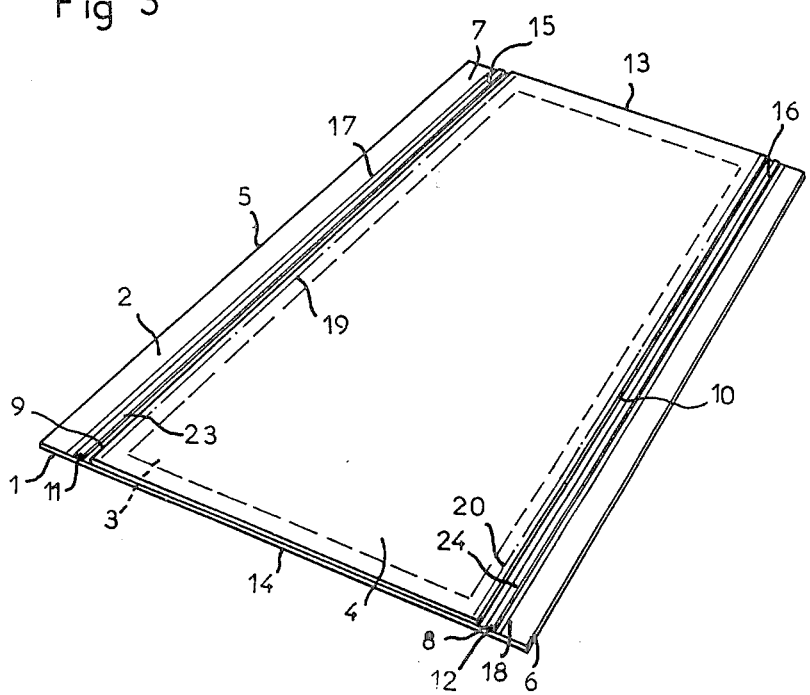
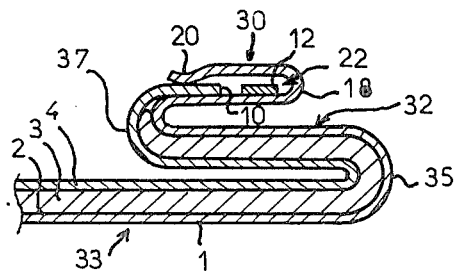

4,210,143

DISPOSABLE NAPPY FOR A BABY

FIELD OF THE INVENTION

The present invention relates to a disposable nappy for a baby.

BACKGROUND OF THE INVENTION

The term "disposable nappy" or "nappy pants" is generally understood to mean a product generally intended to be used once and comprising a sheet of flexible impermeable material such as polyethylene, a flexible pad of absorbent material on one of the sides of this impermeable sheet and generally a sheet of permeable material such as a non-woven textile material covering the pad. The arrangement is generally supplied flat and thus, when flat, is in the shape of a rectangle whereof the longer edges are sometimes cut out in a central area to define a narrow portion, the product also being able to be folded over on itself in the form of a Z in the vicinity of its two longer edges, by folding the side regions onto the area defined by the permeable material. When the product is placed on the baby, the central region which is possibly narrower is placed between the baby's legs and its regions located on either side of this central region are placed respectively in front of and behind the baby, then these two end regions are partly overlapped on the baby's sides where they are interconnected for example by means of self-adhesive tabs. When the nappy is put in position, each of the longitudinal edges of the product overlap on one side of the baby thus defining a loop which constitutes the periphery of a passage for the baby's leg, whereas the transverse edges respectively define the front and rear parts of the waist of the product, which is thus substantially in the form of pants.

A product of this type has numerous variations, but none of these variations overcomes two considerable drawbacks of this product.

The first of these drawbacks consists of an inadequate seal in the region of the thigh. In fact, it is apparent that contact between the central region of the longitudinal edges of the product and the baby's leg is neither sufficiently firm, nor sufficiently flexible to ensure a seal in this region particularly when the baby is moving. Even if care is taken to press this region against the baby's skin when the disposable nappy is put in position, in view of the fact that the pressure applied to the skin should not be excessive, the slightest movement of the baby is sufficient to cause the appearance of an opening causing leakages.

A second drawback of currently known products resides in the fact that even if it is possible to adjust at will the pressure at which the two edges of the product defining the waist are pressed against the baby's skin, this adjustment undertaken at the time of fitting the nappy, does not necessarily prove satisfactory thereafter. In fact, a baby's waist measurement varies rapidly, in practice several times during a day, in particular in the course of digestion. Thus, a waist which is suitably adjusted when the nappy is put in position, may subsequently prove too restricting, for example when the baby eats after the nappy has been put in place, or on the contrary, may prove too wide after a certain period of time for digestion. In the first case, wearing the nappy may become painful for the baby and anyhow, in either case, the disposable nappy does either because the waist tends to reach a narrower part of the body, or because this waist is no longer adequately secured, which on the one hand allows the passages for the legs to open and consequently accentuates the above-mentioned inadequate seal and on the other hand gives the disposable nappy a disorderly shape which is both unattractive and uncomfortable.

SUMMARY OF THE INVENTION

The purpose of the present invention is to propose an improvement which remedies these drawbacks without substantially increasing the cost of the product, which is intended to be thrown away after it has been used once.

To this end, the invention proposes a disposable nappy which before it is used is in the simple form of a rectangle possibly folded over in the form of a Z in the vicinity of each of its longer edges intended to define the periphery of the openings to the leg, by their central part, in manner known per se and also comprising in the vicinity of each of its longer edges, a sheath in which a flexible tie is guided, along this edge, which tie makes it possible to close the openings for the legs to a greater or lesser extent at will, after the disposable nappy has been put in position on the baby in the traditional manner. It should be noted that the user is able to control the tension imparted to the flexible ties for this purpose and that he may also use the disposable nappy in a traditional manner without restricting the openings for the legs after positioning, by means of the flexible ties, depending on the baby's age and size.

However, the use of these flexible ties proves advantageous since firstly it makes it possible to close the disposable nappy in a better manner in the region of the openings for the legs and consequently to reduce the possibility of leakages in this region. This function of the flexible tie is facilitated by the fact that the region of the disposable nappy respectively closest to each of its longitudinal edges is in the form of a flexible flap which can be easily gathered up when one wishes to reduce its apparent length by pulling on the flexible tie. Tightening the periphery of the openings for the legs after putting the nappy on the baby is also advantageous in that it provides a pocket between the baby's legs, due to the looseness of the flexible flaps, which pocket is better suited to accumulating excretions before they are absorbed by the pad, which contributes to preventing leakage of the latter in particular in the region of the openings for the legs.

Furthermore, according to a preferred embodiment of the disposable nappy according to the invention, the parts of the two flexible ties outside the sheath when tightening the periphery of the openings for the legs are joined together in the form of a belt, which eases the pressure on the means for closing the sides of the nappy. Furthermore, in the case of a preferred embodiment where the flexible ties are made from an elastically extensible material, this produces a partially extensible belt which is able to follow the variations in the size of the baby's waist and makes it possible to obtain a constant adjustment of the length of the belt of the nappy to this waist measurement.

The disposable nappy for a baby according to the invention, comprising at least one sheet of flexible impermeable material having two longitudinal edges intended to define openings for the legs and two transverse edges intended to define a waist, and an absorbent pad superimposed on a central region of the impermeable sheet is characterised in that it comprises respectively in the immediate vicinity of each of its longitudinal edges, on either side of the pad, a flexible longitudinal sheath inside which a flexible longitudinal tie is able to slide and in that each sheath comprises means for gaining access to the corresponding flexible tie in order to make it possible to grip the latter manually and tighten it at will, in order to reduce the apparent length of the longitudinal edges, to press the latter at will around the baby's legs and to give the disposable nappy the shape of a trough, between the latter.

BRIEF DESCRIPTION OF THE DRAWINGS

The invention will be better understood on referring to the following description, relating to a non-limiting embodiment as well as to the accompanying drawings which form an integral part of this description.

FIG. 1 is a perspective view of a disposable nappy according to the invention before it is put on the baby.

FIG. 2 is a view of this disposable nappy as fitted on the baby.

FIG. 3 is a perspective view of the disposable nappy in the course of manufacture.

FIG. 4 is a sectional view on line IV—IV of FIG. 1.

DESCRIPTION OF PREFERRED EMBODIMENT

With particular reference to FIGS. 3 and 4, it can be seen that the disposable nappy according to the invention comprises, traditionally, a sheet 1 of flexible impermeable material such as polyethylene, in the shape of a rectangle. Placed on top of one of the sides 2 of this sheet, which side is intended to face the baby, in the central position, is an absorbent pad 3, for example of cellulose wadding, also of rectangular shape but whose dimensions when flat are slightly less than those of the sheet 1. Placed on top of the absorbent pad 3 and sheet 1, on a strip of the latter located over the entire periphery of the pad 3, is a sheet 4 of permeable material such as a non-woven textile material, which has a rectangular shape and dimensions when flat which are between those of the pad 3 and of the sheet 1. During the manufacture of the disposable nappy, the sheet 4 and sheet 1 are connected to each other around the periphery of the absorbent pad 3.

Along the two longer parallel edges 5 and 6 of the sheet 1, an arrangement of this type leaves a longitudinal strip respectively 7 and 8, on the side 2 of the latter which is covered neither by the absorbent pad 3, nor by the permeable sheet 4. A rectilinear flexible tie, respectively 11 and 12 is placed on each of these strips 7 and 8, respectively parallel to the edge 5 and to the edge 6 and in the immediate vicinity of the immediately adjacent edge, respectively 9 or 10 of the permeable sheet 4, the length of which tie is in this case equal to that of the edges 5 and 6.

Depending on the individual case, the flexible tie 11 or 12 may be non-extensible or elastically extensible. Whatever the latter, the tie 11 or 12 is positioned in a rectilinear and loose manner and its ends respectively coincide with the transverse edges 13 and 14 of the sheet 1.

In the case of the embodiment illustrated, the end region of each of the ties 11 and 12, respectively 15 and 16, closest to one of the transverse edges of the sheet 1 and for example the transverse edge 13 of the latter, is connected to the side 2 of the sheet 1 by any means and for example by sticking or welding, the tie otherwise being free over the remainder of its length.

During the manufacture of the disposable nappy, after this positioning of the ties 11 and 12, which may take place continuously on machines manufacturing traditional rectangular nappies, the two strips 7 and 8 are folded over with the side 2 against side 2, about a line respectively 17 and 18 located parallel to the edges 5 and 6 of the sheet 2, respectively between the tie 11 and the edge 5 and further from this edge 5 than from the corresponding edge 9 of the permeable sheet 4 and between the flexible tie 12 and the edge 6 but further from the latter than from the corresponding edge 10 of the sheet 4.

The region of the side 2 of the sheet 1 located between the line 17 and the edge 5 is thus connected to the region of this side 2 located between the lines 17 and 18, along a line 19 parallel to the edge 5 and to the line 17 and chosen such that a region of the sheet 4 located in the vicinity of the edge 9 of the latter is interposed in the region of this line between the two superimposed thicknesses of the sheet 1. Thus, the sheet 4 is connected between the two superimposed thicknesses of the sheet 1 along the line 19. Similarly, a region of the sheet 4 close to the edge 10 of the latter is connected along a line 20 parallel to the edge 6 and to the folding line 18 between the two superimposed thicknesses of the sheet 1 in the vicinity of this edge 6 and this line 18.

The connection along the lines 19 and 20 may be ensured by any known means and for example by welding, or by sticking in particular by means of a hot adhesive mixture known by the name "hot melt".

The lines 19 and 20 are also chosen such that they are respectively located between the edges 9 and 10 of the sheet 4 and the edges of the pad 3 closest to these lines. In other words, the pad 3 is not interposed between the sheets 4 and 1 in the region of the lines 19 and 20, which preserves the flexibility of the regions of the nappy produced in this way and located beyond these lines 19 and 20.

This is particularly apparent in FIGS. 3 and 4.

Folding the sheet 1 over in the vicinity of its edges 5 and 6, respectively along the lines 17 and 18 and the connection of the folded areas respectively along the lines 19 and 20 produces around each of the ties 11 and 12, a longitudinal sheath respectively 21 and 22, parallel to the longitudinal edges of the nappy defined by the folding lines 17 and 18 and inside which the respective regions of the tie 11 and of the tie 12 other than their connection regions 15 and 16, may slide freely.

In order to provide greater access to one region of the flexible ties 11 and 12, respectively 23 and 24, located in the vicinity of the transverse edge 14, in the example illustrated, two notches respectively 25 and 26 have been provided in the immediate vicinity of the lines 17 and 18, close to their intersection with the edge 14, by means of which notches the user is easily able to grasp the region 23 of the tie 11 inside the sheath 21 and the region 24 of the tie 12 inside the sheath 22, in order to apply tension to these regions in a direction respectively away from the connection regions 15 and 16, once the nappy is put in position on the baby.

When means such as adhesive tabs 27 and 28 are provided, in manner known per se, projecting laterally respectively with respect to the line 17 and with respect to the line 18 in the vicinity of the transverse edge 14, the notches 25 and 26 are preferably located respectively between the tab 27 and the edge 14 and between the tab 28 and this edge 14.

The notches 25 and 26 could naturally be replaced by other means for gaining access to the flexible tie inside the corresponding sheath and for example by simple slits provided in the wall of the sheath, i.e. in the sheet 1, for example in the immediate vicinity of the lines 17 and 18 and transversely with respect to these lines.

In manner known per se, the disposable nappy may be supplied in the form illustrated in FIGS. 1 and 4, which show that it is folded in the form of a Z in the vicinity of its two longer edges in order to define five flat surfaces, respectively 29 to 33, connected by folding lines parallel to the lines 17 and 18. There are thus superimposed laterally on a central flat surface 33, with the permeable sheet 4 against the permeable sheet 4, two flat surfaces 31 and 32 connected to this central flat surface 33 along two parallel lines respectively 34 and 35. There are also respectively superimposed on the surface 31 and on the surface 32, with impermeable sheet 1 against impermeable sheet 1, the two flat end surfaces 29 and 30 respectively connected to the intermediate flat surface 31 along the line 36 parallel to the line 34 and to the intermediate flat surface 32 along the line 37 parallel to the line 35.

The distance between the lines 17 and 36, equal to the distance between the lines 18 and 37, is less than the distance between the lines 36 and 34, equal to the distance between the lines 37 and 35, itself less than half the distance between the lines 34 and 35. Preferably, the flat surfaces 29 and 30 are formed exclusively or almost exclusively respectively by the sheaths 21 and 22 and do not include the absorbent pad 3, which stops in the immediate vicinity of the lines 36 and 37 respectively, such that the flat surfaces 29 and 30 are as flexible as possible (c.f. in particular FIG. 4 which illustrates the superimposition of the surfaces 33, 32 and 30).

When the disposable nappy illustrated in FIG. 1 is put in position on the baby, it assumes the shape illustrated in FIG. 2, i.e. the general shape of pants.

In known manner, to this end, the central region 38 of the nappy is placed between the baby's legs, i.e. its region located substantially mid-way between the edges 13 and 14, whilst preserving substantially in this area, the Z-shaped double folds on the sides. The region 39 located between the region 38 and the edge 14 is on the other hand opened out into a flat surface which is best suited to the shape of the baby's back. The region 40 located between the region 38 and the edge 13 is in turn opened out and placed against the baby's front, its corners 41 and 42 being located in the immediate vicinity of the line 13 and respectively of the lines 18 and 17 respectively following the shape of the baby's sides. These corners 41 and 42 on the baby's sides are thus overlapped respectively by the corner 43 located in the immediate vicinity of the intersection of the line 14 with the line 18 and the corner 44 located in the immediate vicinity of the intersection of the line 14 with the line 17, which corners respectively comprise the tabs 28 and 27 whch are thus stuck to the sheet 1 in its part corresponding to the region 40.

During this shaping of the disposable nappy, the edges of the latter respectively defined by the lines 17 and 18 form a loop in their central region, which loops define the openings for the legs such as 45. In this central region, the lines 17 and 18 and the adjacent flat surfaces 29 and 30 come into contact with the baby's legs.

According to the invention, this contact can be made waterproof by means of the flexible ties 11 and 12 whereof the region 23 is engaged by way of the notch 25 and the region 24 by way of the notch 26. The notches 25 and 26 are thus located on the baby's sides, adjacent the front. Since the areas of connection 15 and 16 to the other parts of the disposable nappy ensure the counterpart, a pulling action respectively applied to the areas 23 and 24 towards the front, i.e. in the sense of respectively pulling them out of the sheath 21 and out of the sheath 22, tensions the ties 11 and 12 by the desired amount, with the result of gathering up the two flexible sheaths 21 and 22 and applying them as well as possible, owing to their flexibility, against the baby's legs. The parts of the flat surfaces 29 and 30 other than the sheaths 21 and 22 thus form bellows between these sheaths and the more rigid regions constituted by the surfaces 31, 32 and 33 which contain the absorbent pad 3, which enables the region 33 in particular to move away from the baby's skin in the central region 38, thus forming a trough 46 able to accumulate solid matter and in a temporary manner, liquid matter, until the latter is absorbed by the pad 3 through the sheet 4.

Once the desired degree of tension of the flexible ties 11 and 12 is reached, these ties are immobilised, for example on the sheet 1 in the region 40, i.e. in front of the baby, by any one of their regions removed from the sheaths 21 and 22 at the time of tensioning. In the example illustrated, these regions are knotted at 41, in a bow making it possible to remove the nappy without breaking the flexible tie, but it is also possible to secure the latter on the sheet 1 by suitable means or by the set of tabs 27 and 28, respectively for the region 24 and for the region 23, which thus overlap on the baby's stomach. Other methods of attachment, either to each other, or to the sheet 1, could also be envisaged without diverging from the scope of the invention.

It should be noted that if one adopts the relative position of the tabs respectively 27 and 28 and of the notches respectively 25 and 26 described and illustrated, the two flexible ties 11 and 12 connected to each other and/or to the sheet 1 in the region 40 contribute not only to easing pressure on the connecting tabs 28 and 27 by tending to close the edge 14 around the baby's waist, but also to causing raising of this edge 14 behind the baby, thus facilitating its return to the correct position when the baby straightens up after bending.

Naturally, the disposable nappy according to the invention may have numerous variations, in particular as regards its general structure, which may be of any known type, as regards the construction of the sheaths 21 and 22 guiding the ties 11 and 12 and as regards the method of connection of these ties to the other parts of the nappy. In particular, apart from the connection of the ties at 15 and 16 to the sheet 1, one could envisage a connection to this sheet of their second end, the intermediate region remaining free and accessible through the notches 25 and 26. One could also leave the two ties 11 and 12 free at their two ends, if necessary fixing them to the sheet 1 in a central region of each of the latter, thus providing possibilities of access such as notches 25 and 26 in the vicinity of each of their ends, which would make it possible to place part of the ties 11 and 12 in the form of a partial belt behind the baby, another part constituting part of a belt at the front, as in the example illustrated.

Furthermore, as above-mentioned, it is possible to envisage flexible ties 11 and 12 either in a non-extensible form or in an elastically extensible form.

Instead of folding the disposable nappy in the shape of a Z in the vicinity of each of its longitudinal edges, as described, it is finally possible to envisage other methods of folding and for example folding the latter in three longitudinal flat surfaces as a central flat surface covered internally by an absorbent pad and two more flexible lateral flat surfaces, in particular in the vicinity of the longitudinal edges of the nappy and completely or partly devoid of absorbent pad, these lateral flat surfaces possibly being defined essentially by either of the longitudinal flexible sheaths.

What is claimed is:

1. A disposable nappy for a baby, comprising a sheet of flexible impermeable material having two longitudinal side edges intended to define opening for the legs of a baby and two transverse end edges intended to define a waist portion, an absorbent pad superimposed on a central region of said impermeable sheet with longitudinal side edges of said pad spaced inwardly from longitudinal side edges of said impermeable sheet, the longitudinal side edges of said impermeable sheet being folded inwardly on themselves and secured to said impermeable sheet along longitudinal junction lines at a distance from the folds to form longitudinally extending tubular sheaths at opposite sides of said nappy, said pad being disposed only on a central region of said impermeable sheet between said longitudinal junction lines, a flexible longitudinal tie located inside each of said sheaths and able to slide therein, said nappy being folded over on itself along longitudinal lines to form a central portion, opposite side portions extending inwardly from first fold lines toward a longitudinal center line of said nappy, and opposite edge portions extending outwardly from second fold lines, said edge portions comprising said sheaths, and means providing access to at least one end of each of said longitudinal ties in order to make it possible to grip the latter manually and tension them to reduce the effective length of said sheaths and thereby press the latter around the baby's legs to give the nappy the shape of a trough between said sheaths.

2. A nappy according to claim 1, further comprising a sheet of permeable material covering said pad on the side intended to face the baby, side edge portions of said permeable sheet extending laterally beyond side edges of said pad and secured to said impermeable sheet along said longitudinal junction lines.

3. A nappy according to claim 1 or claim 2, in which said longitudinal ties are elastic.

4. A nappy according to claim 1 or claim 2, in which said ends of said ties are flush with the end of said nappy, said means for providing access to at least one end of each of said ties comprising an opening in said sheath located inwardly from the end of said nappy.

5. A nappy according to claim 1 or claim 2, in which one end of each of said longitudinal ties is secured to said impermeable sheet at one end of said nappy, and in which said means for gaining access to each of said ties comprises an opening in the respective sheath at a location inwardly of the opposite end of said nappy.

* * * * *